(12) United States Patent
Crainich

(10) Patent No.: US 8,906,039 B2
(45) Date of Patent: Dec. 9, 2014

(54) SUTURING DEVICE

(75) Inventor: Lawrence Crainich, Charlestown, NH (US)

(73) Assignee: Design Standards Corporation, Charlestown, NH (US)

( * ) Notice: Subject to any disclaimer, the term of this patent is extended or adjusted under 35 U.S.C. 154(b) by 2301 days.

(21) Appl. No.: 11/386,145

(22) Filed: Mar. 21, 2006

(65) Prior Publication Data

US 2006/0212048 A1  Sep. 21, 2006

Related U.S. Application Data

(60) Provisional application No. 60/663,661, filed on Mar. 21, 2005.

(51) Int. Cl.
*A61B 17/04* (2006.01)
*A61B 17/06* (2006.01)

(52) U.S. Cl.
CPC ... *A61B 17/0469* (2013.01); *A61B 2017/06076* (2013.01)
USPC .......................................................... 606/144

(58) Field of Classification Search
USPC .................................. 606/139, 144, 148, 145
See application file for complete search history.

(56) References Cited

U.S. PATENT DOCUMENTS

| | | | | |
|---|---|---|---|---|
| 4,204,541 | A * | 5/1980 | Kapitanov | 606/145 |
| 4,935,025 | A * | 6/1990 | Bundy et al. | 606/180 |
| 5,018,530 | A * | 5/1991 | Rank et al. | 600/562 |
| 5,353,800 | A * | 10/1994 | Pohndorf et al. | 600/486 |
| 5,356,424 | A * | 10/1994 | Buzerak et al. | 606/223 |
| 5,507,743 | A * | 4/1996 | Edwards et al. | 606/41 |
| 5,545,148 | A * | 8/1996 | Wurster | 604/223 |
| 5,782,844 | A * | 7/1998 | Yoon et al. | 606/139 |
| 5,820,631 | A * | 10/1998 | Nobles | 606/213 |
| 5,830,221 | A * | 11/1998 | Stein et al. | 606/157 |
| 5,947,983 | A * | 9/1999 | Solar et al. | 606/144 |
| 6,015,416 | A * | 1/2000 | Stefanchik et al. | 606/144 |
| 6,071,289 | A * | 6/2000 | Stefanchik et al. | 606/147 |
| 6,280,441 | B1 * | 8/2001 | Ryan | 606/45 |
| 6,315,784 | B1 * | 11/2001 | Djurovic | 606/146 |
| 6,478,776 | B1 * | 11/2002 | Rosenman et al. | 604/164.01 |
| 6,493,591 | B1 * | 12/2002 | Stokes | 607/127 |
| 6,626,917 | B1 * | 9/2003 | Craig | 606/144 |
| 6,663,633 | B1 * | 12/2003 | Pierson, III | 606/148 |
| 6,673,078 | B1 * | 1/2004 | Muncie | 606/104 |
| 7,186,234 | B2 * | 3/2007 | Dahla et al. | 604/22 |
| 2003/0009179 | A1 * | 1/2003 | Craig | 606/139 |
| 2003/0153931 | A1 * | 8/2003 | Schraft et al. | 606/153 |
| 2005/0065505 | A1 * | 3/2005 | Ryan | 606/27 |

* cited by examiner

*Primary Examiner* — Dianne Dornbusch
(74) *Attorney, Agent, or Firm* — Bachman & LaPointe, P.C.

(57) ABSTRACT

A suturing device includes a housing; a helical needle rotatably mounted relative to the housing; and a drive assembly for rotating the needle relative to the housing whereby the helical needle carries a suture through tissue to be sutured. The needle rotates relative to the housing in an axially fixed position and carries a suture for rapid and reliable deployment to close a wound or incision.

18 Claims, 4 Drawing Sheets

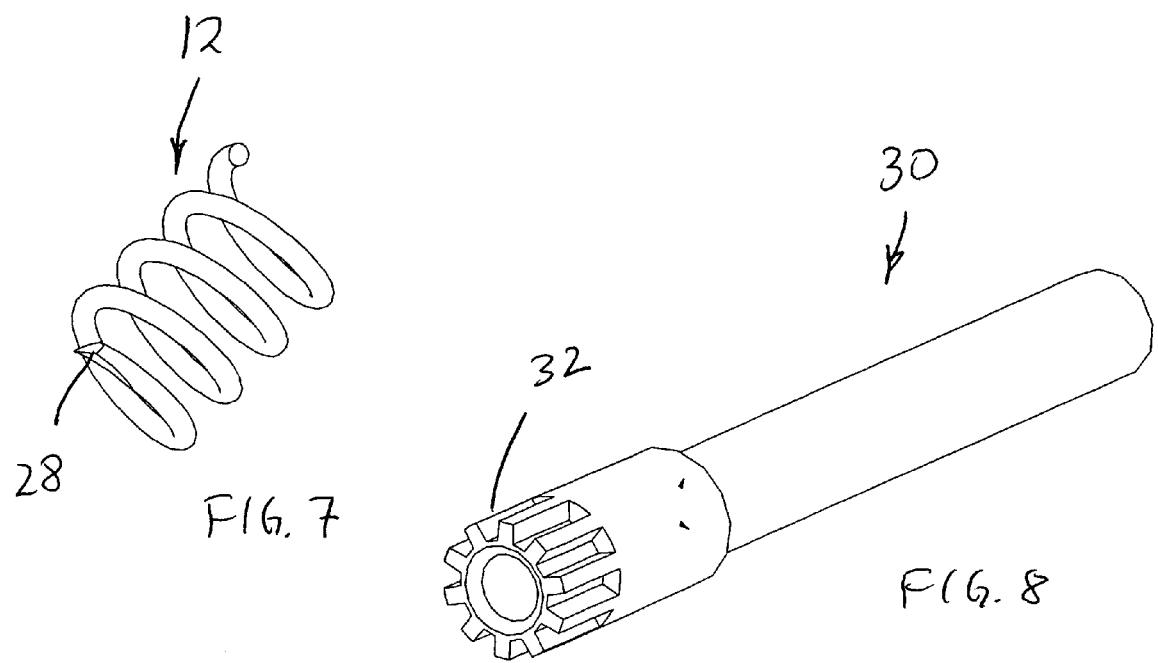
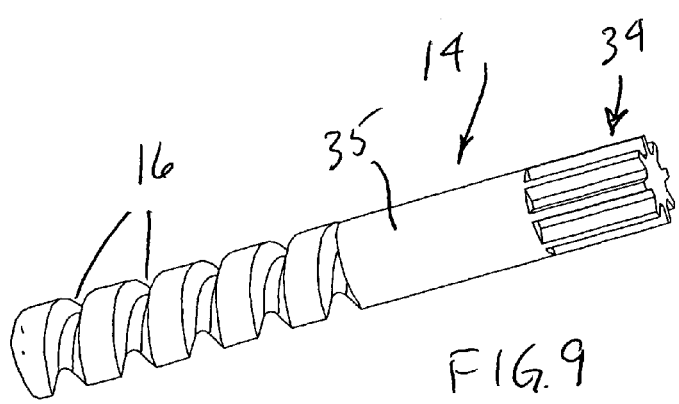

SUTURING DEVICE

REFERENCE TO RELATED APPLICATION

This application claims benefit of provisional application Ser. No. 60/663,661 filed Mar. 21, 2005.

BACKGROUND OF THE INVENTION

The invention relates to suturing and more specifically to a suturing device which can be used to safely and securely suture both open procedures and vascular procedures.

Various approaches are used to suture such procedures. Manual approaches are time intensive and the time taken to close a wound or incision is of course critical.

Mechanical approaches to suturing are not as reliable as would be desired and are also potentially limited in their environments of use.

It is the primary object of the invention to provide a suturing device which is both fast and reliable so that wounds and incisions can be rapidly and securely sutured.

Other objects and advantages of the invention will appear below.

SUMMARY OF THE INVENTION

According to the invention, the foregoing objects and advantages have been attained.

The invention relates to a suturing device having a helical or coiled needle and a drive system which drives the coiled needle with an attached suture. The coiled needle is driven by two shafts positioned on the outside of the coil which have grooves cut into them at the same helix as the needle but in a counter direction. Inside the coil is a partial shaft (half round) that forces or holds the needle in position against and engaged with the outside rollers. The rollers have a roughened or serrated surface as does the outside of the coil. The inside of the coil is smooth as is the needle contact surface of the half round arbor. The friction between the outside of the coil of the needle and the grooves in the driving rollers power the needle rotation. The needle does not advance or retract, but simply rotates in place and positions the suture as desired.

The device can be used with large needles for open procedures as well as with relatively small needles for vascular suturing where the entire device can be deployed through an artery, for example to repair a heart valve where the only invasion would be through an artery in the groin area. Of course, this is an example only and other uses exist well within the scope of the present invention.

Thus, according to the invention, a suturing device is provided which comprises a housing; a helical needle rotatably mounted relative to the housing; and a drive assembly for rotating the needle relative to the housing whereby the helical needle carries a suture through tissue to be sutured.

BRIEF DESCRIPTION OF THE DRAWINGS

A detailed description of the present invention follows with reference to the attached drawings wherein:

FIG. 7 illustrates a helical needle according to the invention;

FIG. 8 illustrates a drive member for an apparatus according to the invention;

FIG. 9 illustrates a drive shaft according to the invention;

DETAILED DESCRIPTION

The invention relates to a suturing device and, more particularly, to a device which can be used to deploy sutures in a wide variety of locations and in a rapid and secure manner.

Figure 1:
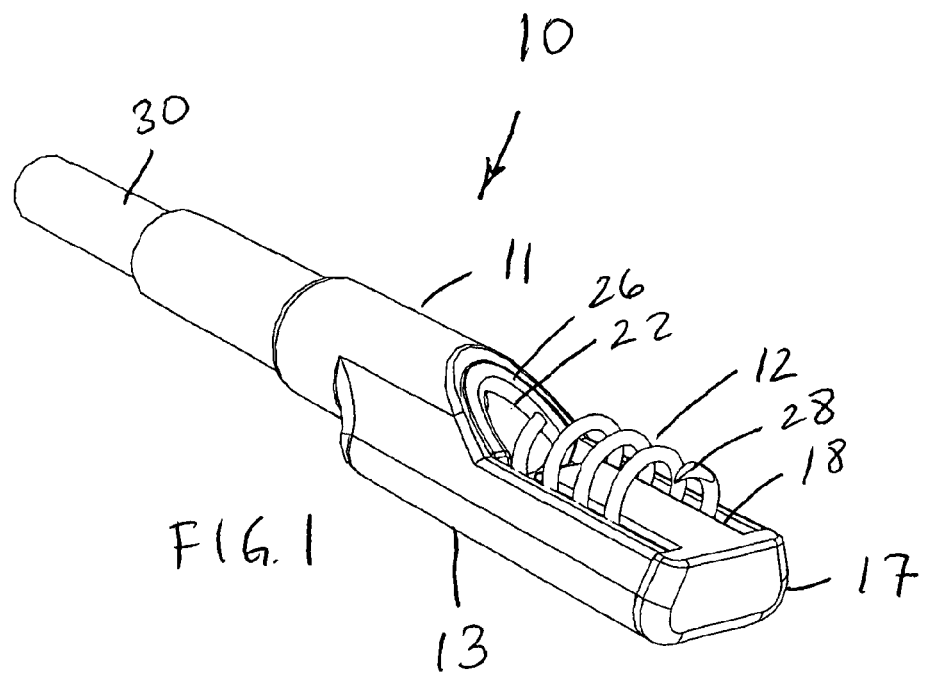
FIG. 1 is a perspective view of a suturing device according to the invention.
Figure 2:
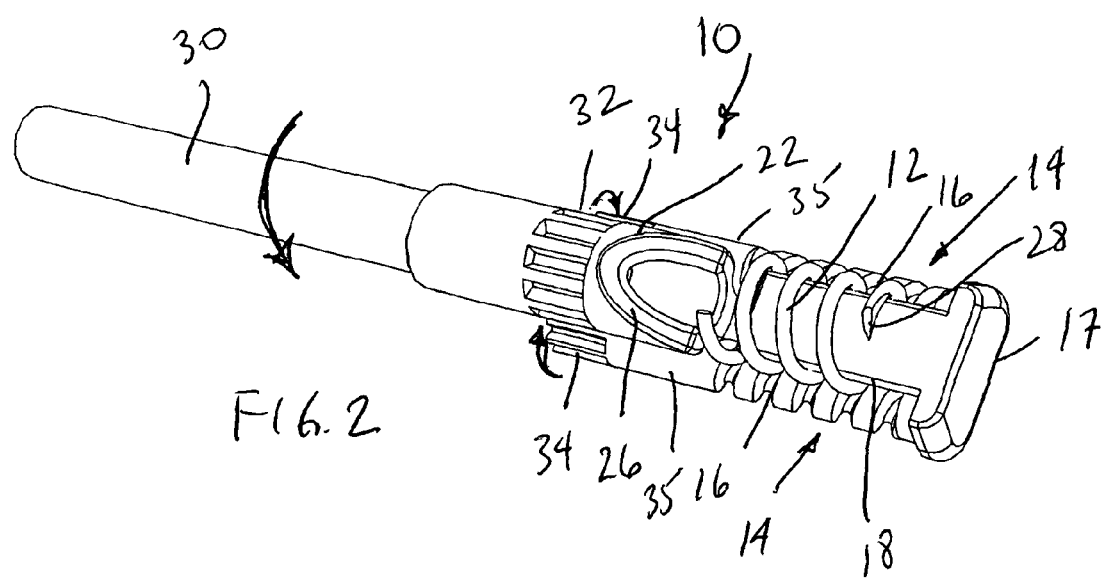
FIG. 2 is a further perspective view of the apparatus of FIG. 1 with the housing removed to illustrate internal components.

Referring to the drawings, FIGS. 1 and 2 illustrate one embodiment of a suturing device 10 according to the invention having a helical or coiled needle 12 and a drive system which drives the coiled needle with an attached suture. A housing 11 of device 10 is illustrated in FIG. 1 and removed in FIG. 2 to show internal structure and components. In this description, ends of the device will be referred to as proximal and distal. As used herein, distal refers to a direction toward the end of device 10, while proximal refers to a direction away from the end of device 10, back along housing 11 and drive member 30.

The coiled needle 12 is in this embodiment driven by two shafts 14 positioned on the outside of the coil which have grooves 16 cut into them at the same helix as the needle but in a counter direction of course, a single shaft or more than two shafts could also be used within the broad scope of the present invention. A drive member 30 discussed further below is engaged with shafts 14 and, as shown by arrows in FIG. 2, can be rotated to result in rotation of shafts 14. Rotation of shafts 14 results in rotation of needle 12 as desired.

Inside the coil is preferably a partial shaft 18 which is also referred to herein as an arbor. Arbor 18 is preferably partial-round, for example half-round, in shape and holds the needle in position against and engaged with the outside shafts 14. The shafts 14 preferably have a roughened or serrated surface, as does the outside of the coil 12, at contact points between same whereby friction between the surfaces is increased so as to assist the shafts 14 in driving helical needle 12 as desired.

The inside of helical needle 12 is preferably smooth as is the needle contact surface or radially outwardly facing surface of the half round arbor or half round shaft 18. Shaft 18 with a smooth or frictionally reduced surface advantageously defines a needle guiding surface which serves to hold needle 12 in place during operation of the device to position a suture as desired. The friction between the outside of the coil of the needle 12 and the grooves in the driving shafts 14 power rotation of the needle when shafts 14 are rotated.

Coiled needle 12 does not advance or retract relative to housing 11 of the device, but simply rotates in place and positions the suture through tissue as desired. Movement of device 10 along the wound or incision allows needle 12 to place the desired suture through both sides of the incision or suture such that, when needle passes beyond the end of the incision or wound, needle can be advanced out of the tissue leaving the desired suture behind.

As shown in the drawings, needle 12, shafts 14 and half round shaft 18 can be positioned within housing 11 and any suitable drive mechanism can be used to impart rotation to shafts 14 as desired. It should be readily apparent that device 10 according to the invention can be used in a wide range of surgical procedures.

In use, a suture can be provided with a T end which can be used for anchoring the suture in tissue. Alternatively, if there is no T end for anchoring, then a multitude of loops can be used to anchor the suture into the tissue.

Device 10 is used to pierce the tissue with 2 or 3 loops and to pull the T end until it anchors. This procedure can be repeated first to lock the sutures in place and then to further secure the suturing as desired.

If sutures are to be used which have no T end, a plurality of loops can first be made to lock the initial suture into the tissue. Device 10 can then be used to form a loop where desired and make a running stitch as needed. Following this, the suture can be tightened so as to complete the suturing.

As with the first case, additional loops can be formed over the initial loops to lock the suture in place, at which time remaining suture can be cut away and the procedure is complete.

It should be appreciated that the suture can be attached to either the proximal or distal end of the needle, and both embodiments are illustrated and described further herein. Further, the drive structure can be reversed, with the driver positioned inside the coil and smooth rollers on the outside, which would be considered well within the scope of the present invention.

Figure 3:
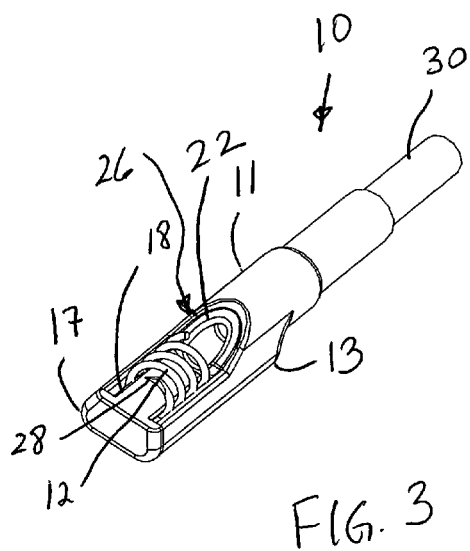
FIG. 3 is a further perspective view of an apparatus according to the invention.

FIG. 3 further illustrates the embodiment of the present invention as illustrated in FIGS. 1 and 2, wherein device 10 has a housing 11 rotatably supporting a helical needle 12 as discussed above. Needle 12 is preferably rotatable relative to housing 11 while being held against axial displacement relative to housing 11. Separate components of device 10 are discussed below and separately illustrated in FIGS. 4-9.

Figure 4:
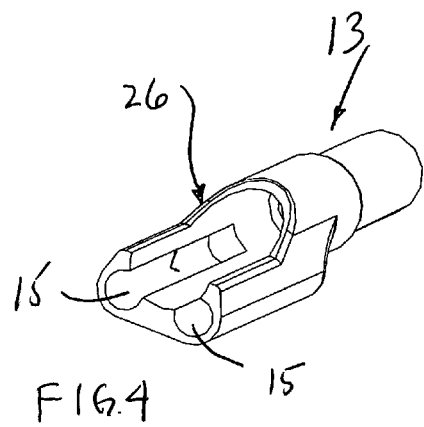
FIG. 4 is a perspective view of a portion of the housing of the embodiment of FIG. 3.

FIG. 4 separately illustrates a housing body 13 according to the invention. Body 13 has an internal passage for accommodating a drive member as will be discussed further below, and also preferably defines rotation chambers 15 for rotatably receiving shafts 14. Body 13 preferably has a rounded proximal end as shown to facilitate use in laparoscopic procedures and the like. As shown, rotation chambers 15 are advantageously substantially parallel to each other and spaced around a circumference of helical needle 12 so as to support and stabilize helical needle 12 through shafts 14.

Figure 5:
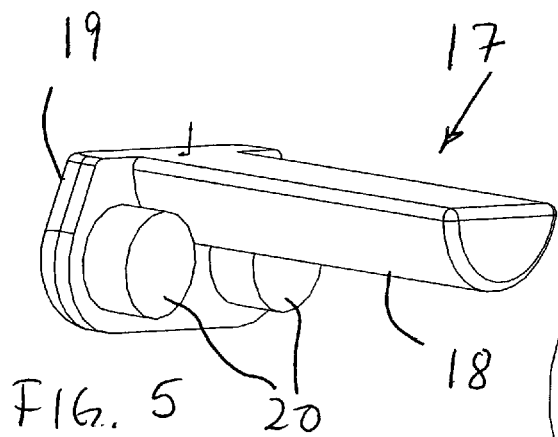
FIG. 5 is a perspective view of a portion of the housing of the embodiment of FIG. 3.

FIG. 5 illustrates an end cap member 17 which can be included in housing 11 according to the invention. End cap member 17 advantageously cooperates with body 13 to complete rotation chambers 15 and also can define half round shaft or arbor 18 as discussed above to provide a desired needle support surface. End cap member 17 preferably further has an end plate 19 which can be sized to smoothly cover the end of body 13 as shown for example in FIG. 3.

Proximally extending structures 20 can be positioned on end cap member 17 as shown in FIG. 5, and structures 20 can be sized to extend into rotation chambers 15 so as to rigidly mount end cap member 17 relative to body 13 as desired.

Figure 6:
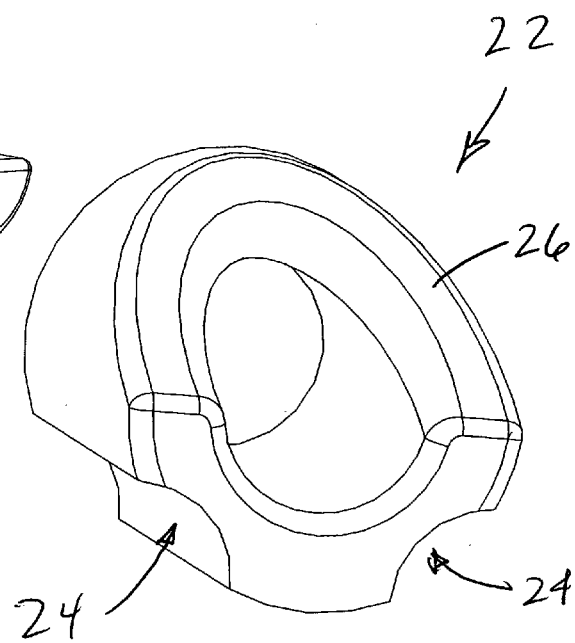
FIG. 6 is a perspective view of a portion of the housing of the embodiment of FIG. 3.

FIG. 6 shows a hub 22 which can also form a part of housing 11 according to the invention. As shown, hub 22 is advantageously a substantially ring shaped member and defines outward partial-round surfaces 24 which form a portion of rotation chamber 15 for shafts 14 as discussed above. Hub 22 also preferably is sized to fit circumferentially within housing 11. Further, hub 22 can be provided with a sloped distally facing sloped surface 26 which is positioned to coincide with a similarly sloped surface of housing 11, in this case defined on body 13. These surfaces coincide and are preferably positioned proximal of helical needle 12 such that there is a smooth transition from the zone of needle 12 to an outside zone of housing 11. According to this embodiment of the invention, hub 22 is a separate piece from body 13. Alternatively, these pieces of housing 11 can be formed as a single part if desired.

FIG. 7 illustrates a needle 12 according to the invention, which can be a simple helical structure having a sharp tip 28 at one end. Needle 12 can be used to carry a suture in a manner known to a person skilled in the art so that the suture is positioned as desired relative to a wound and/or surgical incision when needle 12 is passed through both sides of the wound or incision while carrying the suture. Subsequent rotation of needle 12 relative to housing 11 brings the suture with it and thereby closes the wound or incision as desired, and the procedure is complete when the apparatus has traversed the entire length of the wound or incision.

It should be appreciated that various shape tips can be used with needle 12.

FIG. 8 further illustrates a driver member 30 for use in driving shafts 14 of device 10 according to the invention. Drive member 30 preferably is provided as a substantially round member rotatably relative to housing 11 and engaged with shafts 14 such that rotation of drive member 30 relative to housing 11 causes rotation of shafts 14 relative to housing 11. Drive member 30 can advantageously be provided as a shaft rotatable relative to body 13, preferably rotatable within body 13, and having a series of teeth 32 at a distal end thereof. Referring also to FIG. 9, a preferred shaft 14 is illustrated. As shown, shaft 14 can be provided having a toothed end 34, preferably facing proximally. Teeth 32 of drive member 30 can be engaged with toothed end 34 of each shaft 14 such that rotation of a single drive member 30 can drive a plurality of shafts 14 according to the invention.

Still referring to FIG. 9, shafts 14 preferably have a substantially smooth section 35 which is located substantially half way along same, and grooves 16 or threads which advantageously serve to drive rotation of helical needle 12 relative to housing 11 when drive member 30 is rotated relative to housing 11.

In the embodiment discussed above, needle 12 is positioned with sharp tip 28 facing the distal end of device 10, and in use device 10 will need to be moved in that direction along an incision or wound to be sutured or closed.

Figure 10:
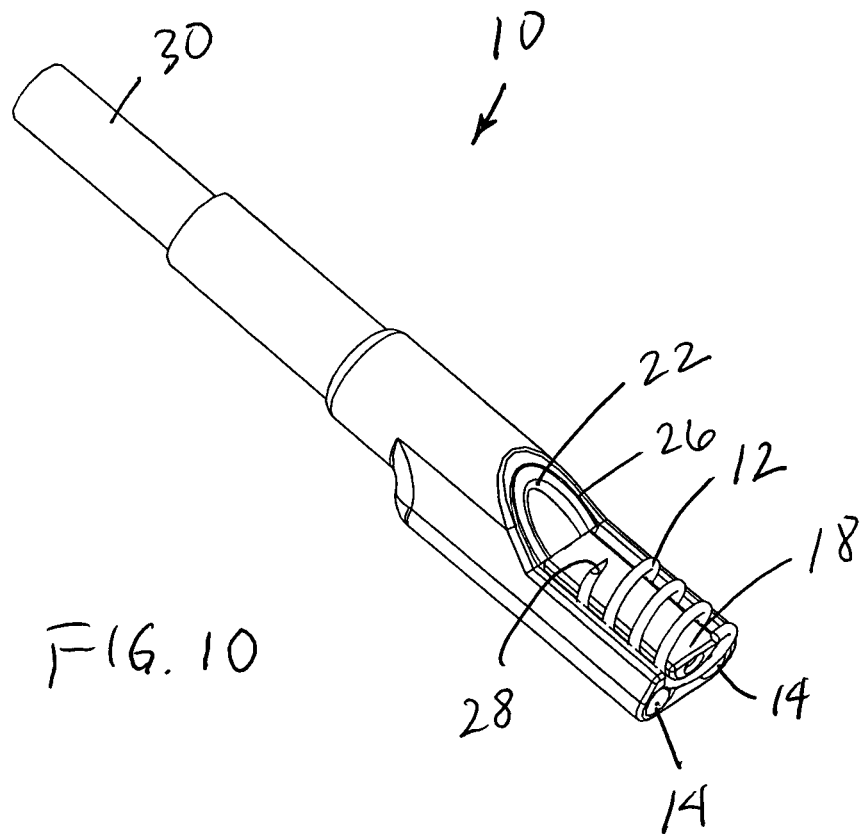
FIG. 10 illustrates an alternate embodiment of the invention wherein the needle has a sharp tip which faces proximally on the device.
Figure 11:
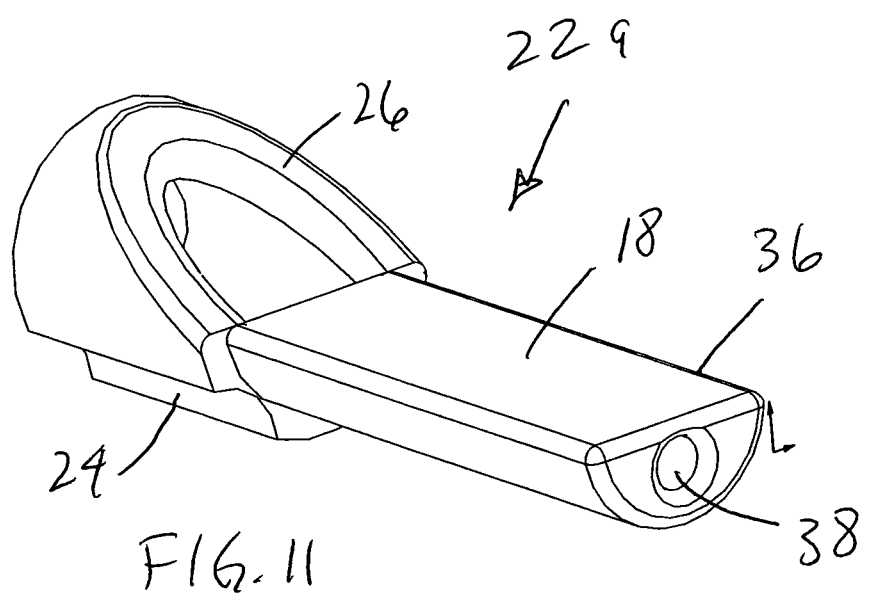
FIG. 11 illustrates an alternate housing component which is preferred for the embodiment of FIG. 10.

FIG. 10 illustrates an alternative embodiment wherein needle 12 is positioned with sharp tip 28 facing proximally. In use with this embodiment, device 10 is moved proximally along a wound or incision to be closed. Device 10 of FIG. 10 can be provided with similar components to those discussed above in connection with the embodiment of FIG. 3. Alternatively, and as shown in FIG. 11, housing 11 can have different components and structure. For example, hub 22a in this embodiment can have a distally extending structure 36 which defines arbor 18, that is, the smooth surface about which helical needle 12 rotates. Structure 36 can be provided having a passage 38 passing through same as illustrated to allow sutures or other probes, guides or the like to be deployed through structure 36 and out of the distal end of the apparatus. Further, in this embodiment, no end cap member 17 is needed.

It should be appreciated that device 10 according to the invention can be produced at different scales for use in different types of procedures. For external procedures, device 10 can be relatively large if desired for a particular use. For laparoscopic procedures, device 10 according to the invention is advantageously sized to fit within a typical cannula for carrying out a desired procedure.

Device 10 can also be provided with housing 11 made from a suitable material based upon the intended use. Thus, material for device 10 according to the invention should be selected based upon environment of use, whether device 10 is to be sterilized and re-used, and the like.

It should also be appreciated that this disclosure is made in terms of preferred embodiments of the invention which are intended to be illustrative, and not limiting, upon the broad scope of the invention which is defined by the appended claims.

The invention claimed is:

1. A suturing device, comprising:
a housing;
a helical needle rotatably mounted relative to the housing; and
a drive assembly for rotating the needle relative to the housing whereby the helical needle carries a suture through tissue to be sutured, wherein the housing comprises a needle guide positioned to guide rotation of the needle relative to the housing, and wherein the needle guide comprises a partial-round structure positioned within the helical needle such that the needle is coiled around the needle guide and wherein the housing further comprises an end plate extending radially from a distal end of the needle guide, and extending beyond a circumference of the needle.

2. The device of claim 1, wherein the housing has a distal end and a proximal end, wherein the helical needle has a sharp tip at one end, and wherein the helical needle is arranged relative to the housing with the sharp tip at the distal end.

3. The device of claim 1, wherein the housing has a distal end and a proximal end, wherein the helical needle has a sharp tip at one end, and wherein the helical needle is arranged relative to the housing with the sharp tip at the proximal end.

4. The device of claim 1, wherein the drive assembly comprises a plurality of shafts positioned at different locations around a circumference of the helical needle.

5. The device of claim 4, further comprising a single rotatable drive member engaged to drive each of the plurality of shafts.

6. The device of claim 5, wherein the housing defines a plurality of rotation chambers for rotatably holding each of the shafts, and further defines a drive member chamber for rotatably holding the drive member.

7. The device of claim 6, further comprising an end cap member for closing off each of the plurality of rotation chambers.

8. The device of claim 5, further comprising a hub positioned within the housing and defining a plurality of outer partial round surfaces for supporting the plurality of shafts within the plurality of rotation chambers.

9. The device of claim 1, wherein the helical needle is rotatable relative to the housing in an axially fixed position.

10. A suturing device, comprising
a housing;
a helical needle rotatably mounted relative to the housing; and
a drive assembly for rotating the needle relative to the housing whereby the helical needle carries a suture through tissue to be sutured, wherein the drive assembly comprises a plurality of shafts engaged with the helical needle and rotatable relative to the housing whereby rotation of the shaft rotates the helical needle relative to the housing, wherein the plurality of shafts are positioned at different locations around and contacting an outer circumference of the helical needle, and further comprising a single rotatable drive member engaged to drive each of the plurality of shafts.

11. The device of claim 10, wherein the housing comprises a needle guide positioned to guide rotation of the needle relative to the housing.

12. The device of claim 11, wherein the needle guide comprises a partial-round structure positioned within the helical needle.

13. The device of claim 10, wherein the shafts and the helical needle have serrated contacting surfaces to increase friction between them.

14. The device of claim 10, wherein the shaft comprises a threaded member having threads engaged with the helical needle.

15. The device of claim 10, wherein the housing defines a rotation chamber for rotatably holding the shaft.

16. The device of claim 15, further comprising an end cap member for closing off an end of the rotation chamber.

17. The device of claim 10, wherein the single rotatable drive member engages each of the plurality of shafts at a proximal portion of the housing.

18. the device of claim 10, wherein the single rotatable drive member is directly engaged with each of the plurality of shafts.

* * * * *